United States Patent
Li et al.

(10) Patent No.: US 7,054,407 B1
(45) Date of Patent: May 30, 2006

(54) METHODS AND APPARATUS TO FACILITATE RECONSTRUCTION OF IMAGES

(75) Inventors: Jianying Li, New Berlin, WI (US); Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/053,762

(22) Filed: Feb. 8, 2005

(51) Int. Cl.
*H05G 1/26* (2006.01)

(52) U.S. Cl. .......................................... 378/16; 378/8
(58) Field of Classification Search ................ 378/16, 378/4, 109–110, 62, 5, 8
See application file for complete search history.

(56) References Cited

U.S. PATENT DOCUMENTS 6,307,918 B1 * 10/2001 Toth et al. .................. 378/158
6,490,337 B1 * 12/2002 Nagaoka et al. .............. 378/20

\* cited by examiner

*Primary Examiner*—David V. Bruce
*Assistant Examiner*—Hoon Song
(74) *Attorney, Agent, or Firm*—Carl B. Horton, Esq.; Armstrong Teasdale LLP

(57) ABSTRACT

A methods and apparatus for reconstructing images are provided. The apparatus includes a CT imaging system configured to scan an anatomy to acquire path-length information, determine at least one threshold value using the acquired path length information, dynamically adjusting the threshold based on clinical applications and scan parameters, and perform a low signal correction on data obtained from scanning the anatomy using the determined threshold value.

27 Claims, 5 Drawing Sheets

METHODS AND APPARATUS TO FACILITATE RECONSTRUCTION OF IMAGES

BACKGROUND OF THE INVENTION

This invention relates generally to methods and apparatus for reconstructions of images in computed tomography (CT), and more particularly to methods and apparatus for maintaining artifact free images with high spatial resolution for normal dose scans while providing adequate correction for low dose scans.

In at least some computed tomograph (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a post patient collimator for collimating scattered x-ray beams received at the detector. A scintillator is located adjacent the post patient collimator, and photodiodes are positioned adjacent the scintillator.

Multislice CT systems are used to obtain data for an increased number of slices during a scan. Known multislice systems typically include detectors generally known as 3-D detectors. With such 3-D detectors, a plurality of detector elements form separate channels arranged in columns and rows. Each row of detectors forms a separate slice. For example, a two slice detector has two rows of detector elements, and a four slice detector has four rows of detector elements. During a multislice scan, multiple rows of detector cells are simultaneously impinged by the x-ray beam, and therefore data for several slices is obtained.

Because different CT applications require different image quality, physicians may use very low scan techniques for certain CT applications such as low dose lung screening, and CT localization scans for PET applications. In such applications, high image spatial resolution can be traded off with the lower scan dose. However, organ boundaries should be well delineated, high-density blood vessels and tumors should be visualized and streaking artifacts should be minimized.

At least some known adaptive pre-smoothing algorithms used in normal dose applications fail to provide adequate correction for these extremely low dose applications. In the CT localization scans for PET applications a post-smoothing operation may be performed on images to obtain certain noise characteristics. However, such post-smoothing may introduce residual streaking artifacts and over-smoothness when the scans are acquired with low CT dose.

BRIEF DESCRIPTION OF THE INVENTION

In one embodiment, an apparatus for reconstructing images is provided. The apparatus includes a CT imaging system configured to scan an anatomy to acquire path-length information, determine at least one threshold value using the acquired path length information, dynamically adjusting the threshold based on clinical applications and scan parameters, and perform a low signal correction on data obtained from scanning the anatomy using the determined threshold value.

In another embodiment, a computer program embodied on a computer readable medium for performing a CT imaging scan is provided. The computer program includes a code segment programmed to control a CT imaging system to scan an anatomy to acquire path-length information, determine at least one threshold value using the acquired path length information, and perform a low signal correction on data obtained from scanning the anatomy using the determined threshold value.

In yet another embodiment, a method for obtaining data is provided. The method includes scanning an anatomy to acquire path-length information, determining at least one threshold value using the acquired path length information, and performing a low signal correction on data obtained from scanning the anatomy using the determined threshold value.

DETAILED DESCRIPTION OF THE INVENTION

Figure 1:
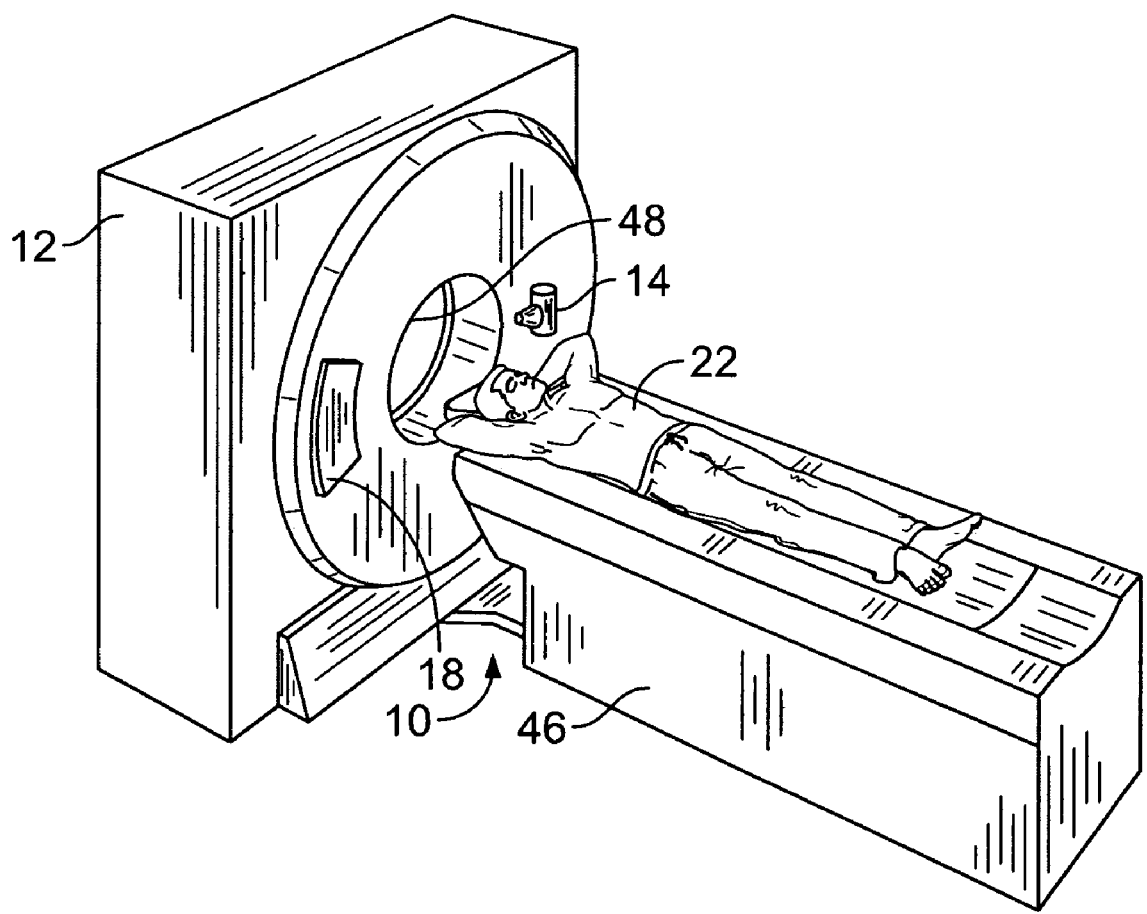
FIG. 1 is a pictorial view of a multi slice volumetric CT imaging system 10.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

To further reduce the total acquisition time, multi-slice CT has been introduced. In multi-slice CT, multiple rows of projection data are acquired simultaneously at any one instant. When combined with helical scan mode, the system generates a single helix of cone beam projection data. Thus, a volumetric CT three-dimensional (3D) image of a scanned object can be generated.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 2:
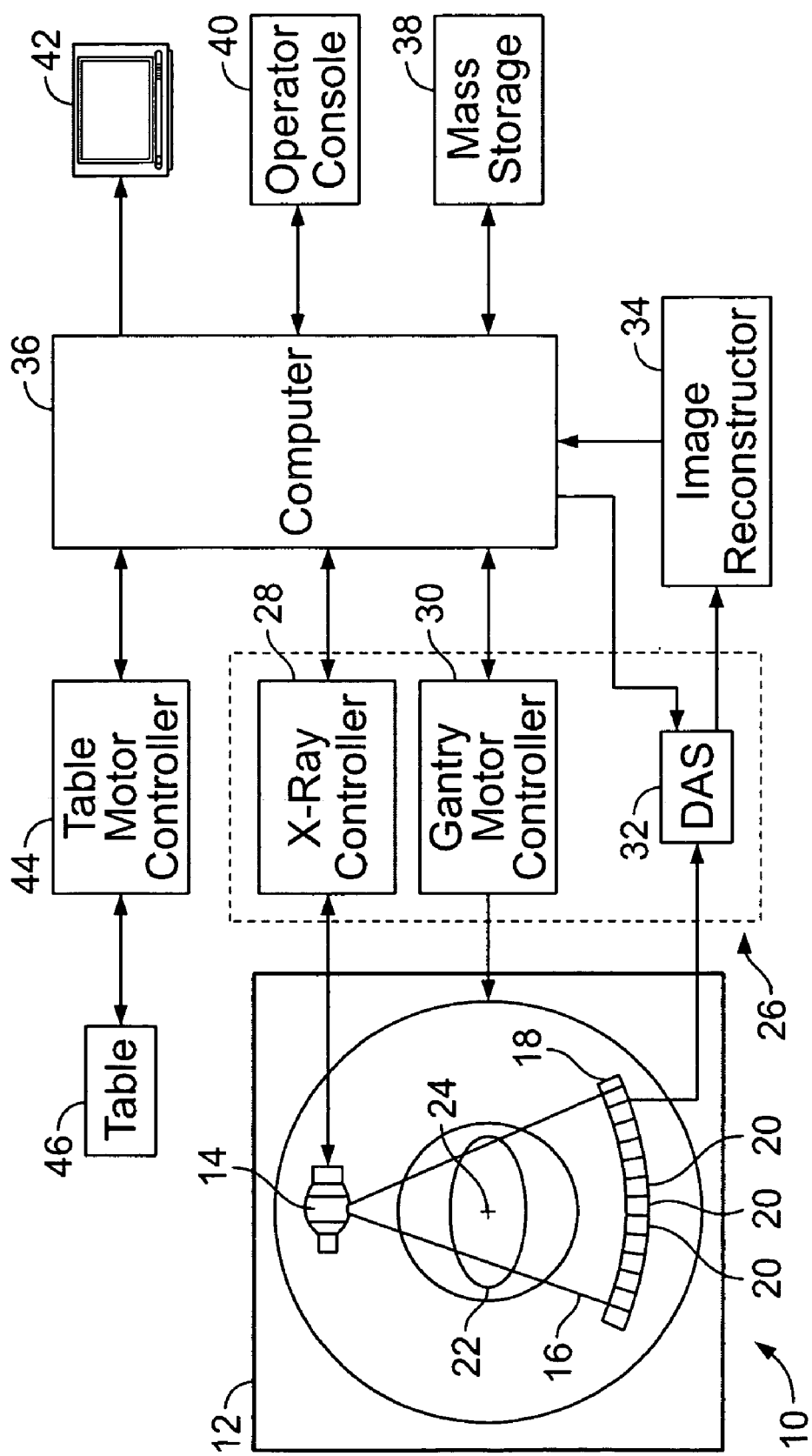
FIG. 2 is a block schematic diagram of the system illustrated in FIG. 1.

FIG. 1 is a pictorial view of a multi slice volumetric CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Application and acquisition dependent threshold selection for the pre-smoothing algorithms for CT is described herein. Such threshold selection facilitates generation of artifact-free images with high spatial resolution for normal dose CT scans and adequate correction for extremely low dose CT applications such as Lung Screening, Perfusion and CT localizations for PET application. The thresholds may be dynamically adjusted based on clinical applications and scan parameters. At least one herein described method combines both the path-length information from two orthogonal views and an application-dependent parameter to automatically determine the set of thresholds for low signal correction. The application-dependent parameter can be linked to either scan protocols or to buttons on the graphic user interface (GUI). It can also be adjusted by the tube current settings during the scan for the cardiac motion- or respiratory motion-driven scans. The path-length information is obtained real time based on the measurement from the previous rotation. Once the thresholds are determined, different smoothing kernels may be selected to be associated with the different thresholds. To avoid over-smoothing, higher degree smoothing operations are only turned on when lower thresholds are triggered. Finally, the smoothing can be modulated by a smoothing gain factor, which is a function of projections themselves.

In addition, the amount of projection smoothing also depends on the acquisition and reconstruction. For dose reduction, x-ray tube current is modulated according to the amount of attenuation of the scanned object. For example, when scanning shoulder regions, x-ray tube current near A–P orientation is significantly lower than the lateral orientation due to the longer path length across the shoulders. Consequently, one could incorporate this knowledge in the projection filter design in terms of threshold and the amount of smoothing. Consequently, this modification of bowtie filter shape could be incorporated in the projection filter design. Specifically, one herein described method performs the following steps:

(1) Projections are first prepped until just before a known logarithmic operation. Assuming a scan starts at 0 degrees. For the first rotation, the method averages the lowest N (typical value of N is 5) prepped projection PP at 0 degree (PP1) and 90 degree (PP2). For rotation M (M>1), the two averaged values are determined at 270+(M−2)*360 and (M−1)*360 degrees, respectively.

(2) At least one threshold can then be determined using the following equation:

$$Sth = A*(PP1*PP2)^B \quad (1)$$

where Sth is a threshold, PP1 and PP2 are the averaged values of the prepped projections at the described angular views, and A and B are constants. A typical value of B is 0.41 and A is an adjustable parameter linked to different applications. For CT scans with normal dose, a typical A value is 0.165, and for lower dose applications such as low dose Lung screening, the A value could be greater than 0.5.

(3) To avoid over-smoothing for very small object, the determined threshold will then be modulated based on the value of the threshold itself and eventually truncated to a fixed value. An example of modulation curve for Sth range from 0.005 to 0.052 can be expressed in the following equation. Values greater than 0.052 will be truncated to 0.026.

$$S\_gain = 1.1437 - 32.2*Sth + 725.0*Sth^2 - 6612.0*Sth^3 \quad (2)$$

$$Sth = A*(PP1*PP2)^B*S\_gain \quad (3)$$

(4) From Sth, a set of threshold can then be determined that have different smoothing lengths and kernels associated with them:

$$Sth\_u = Sth*4.0$$

$$Sth\_m = Sth*0.3$$

$$Sth\_l = Sth*0.08 \quad (4)$$

Based on the determined thresholds, smoothing operations are then performed on the prepped projection. Different degrees of smoothing can be used based on which of the pre-selected thresholds was triggered. In addition, the smoothing operation can be directional and adaptive. That is, the smoothing operation can be applied in the direction where no anatomy structure boundary is detected. Alternatively, a sample that is significantly different than other samples can be excluded from the smoothing.

To dynamically adjust the projection filtering to account for the "smart mA" feature (tube current changes dynamically during scanning), the x-ray tube current curve (currently stored in the projection header) can be used to modify the threshold and the amount of filtering on a view by view basis. In one embodiment, the threshold, Sth, is scaled by the real time x-ray tube current, c. For example, on one embodiment, c is calculated in accordance with:

$$Sth = S_f \left(\frac{c_f}{c}\right)^a \quad (5)$$

where $S_f$ is the threshold determined using the path-length information, $c_f$ is a reference tube current, and $\alpha$ is a parameter. The value of Sth can also be expressed as a function of $S_f$, $c_f$ and c in terms of polynomial expressions. When the x-ray tube current is less than the reference tube current value, the threshold value increases so that the filtering will be performed at a higher projection value before (−log). This means that filtering will be performed for a smaller path length. Similarly, the amount of smoothing will also vary with the $c_f/c$ ratio.

To account of the dynamic bowtie filtering, both the threshold and the filtering function could be functions of the detector channel and projection view. Note that in the bowtie design wherein the bowtie shape changes dynamically to best fit the patient profile to reduce x-ray dose, the total path length of attenuation depend not only on the scanned object itself, but also on the bowtie path-length for that particular projection sample.

The herein described methods, system, and software have been evaluated using extremely low dose CT scans, including the 5 mAs low dose lung scan, and low dose CT scan for PET application. In the low dose lung scan case, the application-dependent algorithm delivered extra correction to provide almost streaking artifact-free images; and in the PET/CT application case, the herein described methods, system, and software not only eliminated the streaking artifacts that are evident in the images obtained using the current method that performs the post smoothing, but also provided sharper images and images with better defined organ boundaries.

Figure 3:
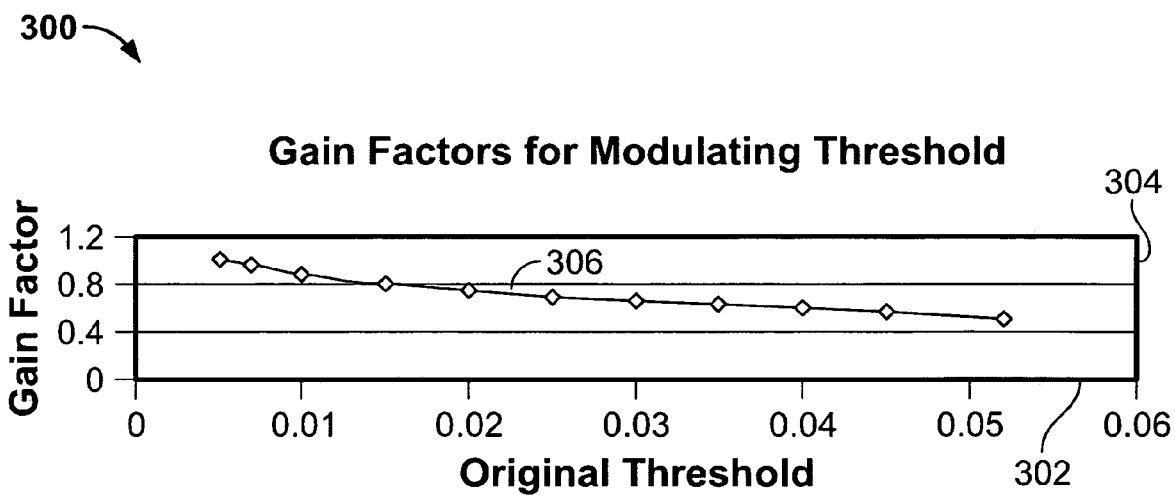
FIG. 3 illustrates an example of a threshold modulation factor as a function of a plurality of original thresholds.

FIG. 3 illustrates an exemplary graph 300 of a threshold modulation factor as a function of a plurality of original thresholds. Graph 300 includes an x-axis 302 graduated in units of original threshold value and a y-axis 304 that is graduated in units of gain factor. A trace 306 illustrates an exemplary relationship between original threshold value 302 and gain factor 304.

Figure 4:
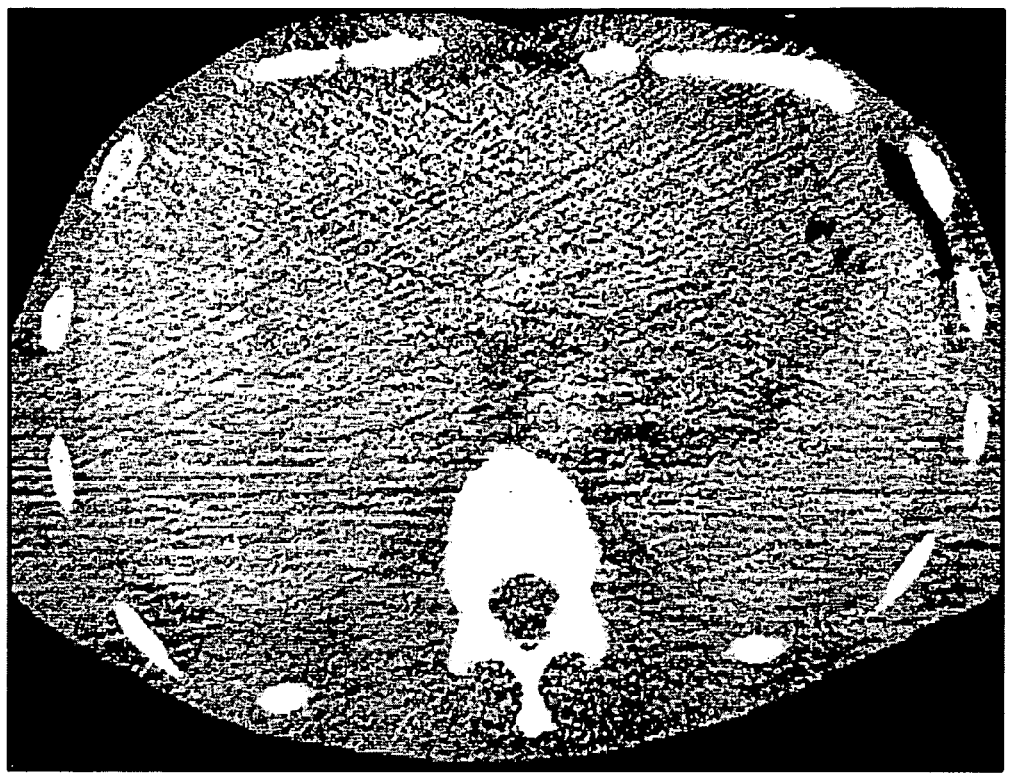
FIG. 4 illustrates an image with a known algorithm producing the image.
Figure 5:
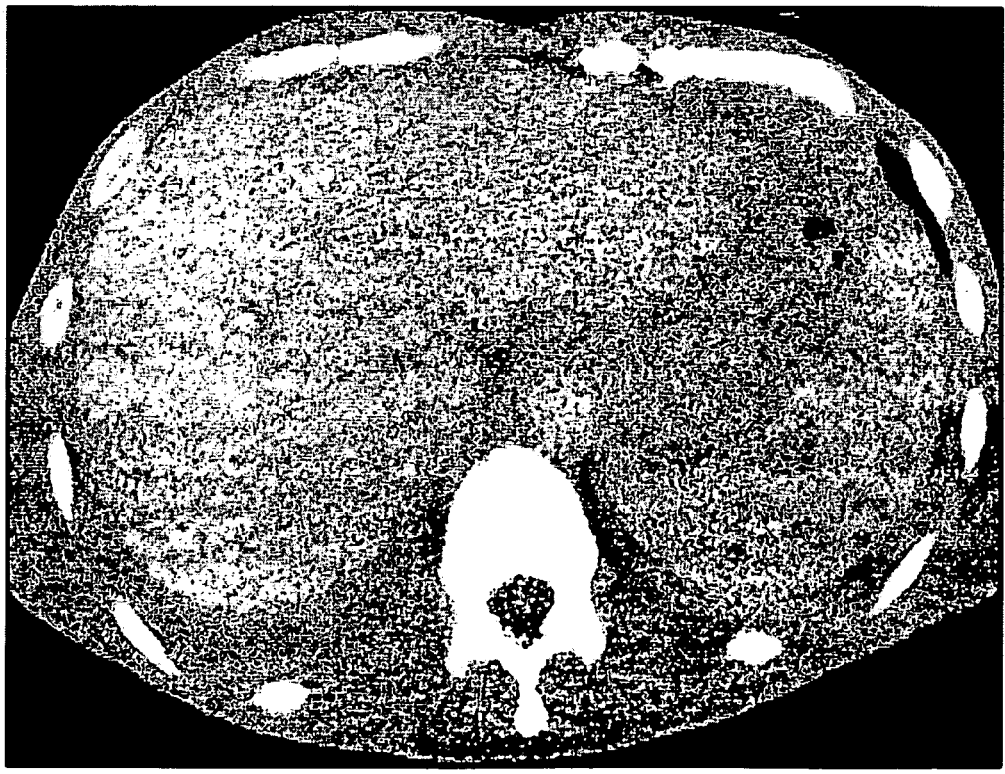
FIG. 5 illustrates an image with the herein described methods producing the image.

FIGS. 4 and 5 illustrate an image comparison with a known algorithm producing the image in FIG. 4 and the herein described methods producing the image in FIG. 5. Both FIGS. 4 and 5 are simulated low dose scans to represent CT localization scan for PET application.

Figure 6:
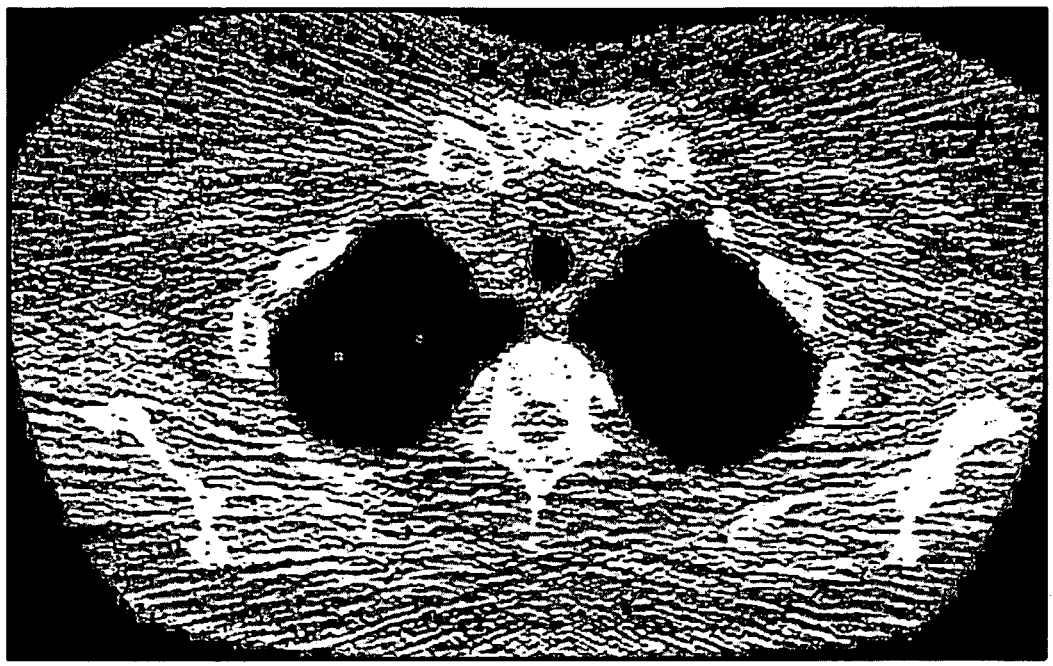
FIG. 6 illustrates an image with a known algorithm producing the image.
Figure 7:
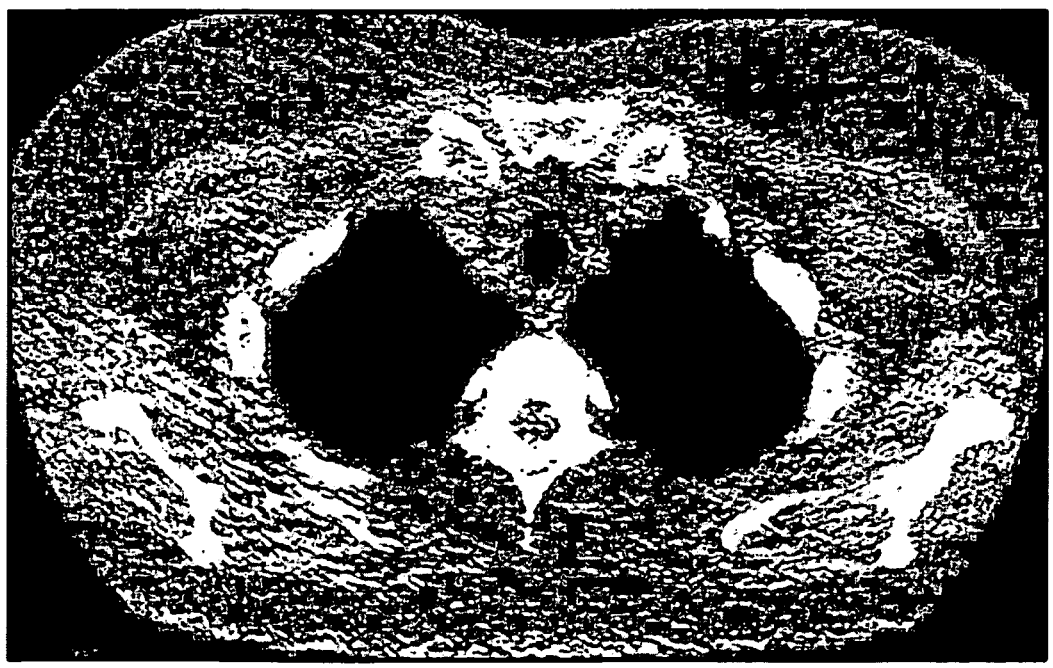
FIG. 7 illustrates an image with the herein described methods producing the image.

FIGS. 6 and 7 illustrate an image comparison with a known algorithm producing the image in FIG. 6 and the herein described methods producing the image in FIG. 7. The application-dependent algorithm provided additional correction to provide almost streaking artifact-free images.

Technical effects include an automated detection of lung nodules and colon polyps with very little false positives and high sensitivity. False positive reduction using complementary responses incurs no additional computation cost and provides a dramatic reduction of false response. Innovative mirrored Look Up Table (LUT) allows user flexibility to control the response values to be displayed for cylindrical and spherical responses simultaneously. Extremely fast processing time due to the 2 pass approach: for a 500 slices acquisition (near isotropic data: 0.625 mm slice thickness) on a standard AW, the first filtering step takes less than 5 seconds, the second multiple segmentation step takes between twenty and forty seconds depending on the amount of found candidates after the first step. This is up to several orders of magnitude faster than all published data. Processing time can even be further reduced based upon rough processing criteria. Increased productivity for the radiologist, decreased reading time. Improves sensitivity in detecting lesions and lowers variability in detected lesions amongst radiologists.

The above-described embodiments of an imaging system provide a cost-effective and reliable means for examining a patient. More specifically, the imaging system facilitates maintaining artifact free images with high spatial resolution for normal dose scans while providing adequate correction for low dose scans.

Exemplary embodiments of imaging system methods and apparatus are described above in detail. The imaging system components illustrated are not limited to the specific embodiments described herein, but rather, components of each imaging system may be utilized independently and separately from other components described herein. For example, the imaging system components described above may also be used in combination with different imaging systems.

While the invention has been described in terms of various specific embodiments, those skilled in the art will recognize that the invention can be practiced with modification within the spirit and scope of the claims.

What is claimed is:

1. A CT imaging apparatus configured to:
   scan an anatomy to acquire path-length information;
   determine at least one threshold value using the acquired path length information:
   dynamically adjusting the threshold value based on clinical applications and scan parameters; and
   perform a low signal correction on data obtained from scanning the anatomy using the determined threshold value.

2. A CT imaging apparatus in accordance with claim 1 wherein said apparatus is further configured to scan an anatomy to acquire path-length information from at least two orthogonal views.

3. A CT imaging apparatus in accordance with claim 2 further configured to:
   receive at least one application dependent parameter; and
   determine the at least one threshold value using the acquired path length information and the received application dependent parameter.

4. A CT imaging apparatus in accordance with claim 1 further configured to adaptively scale the determined threshold based on a dynamically changing x-ray tube current.

5. A CT imaging apparatus in accordance with claim 1 further configured to perform a low signal correction on data obtained from scanning the anatomy using the determined threshold value, wherein the low signal correction is directionally adaptive.

6. A CT imaging apparatus in accordance with claim 5 further configured to adaptively scale the determined threshold based on a dynamically changing x-ray tube current.

7. A CT imaging apparatus in accordance with claim 1 further configured to perform a low signal correction on data obtained from scanning the anatomy using the determined threshold value, wherein the low signal correction is adaptive to a presence or absence of an anatomy boundary.

8. A CT imaging apparatus in accordance with claim 7 wherein the low signal correction is also directionally adaptive.

9. A CT imaging apparatus in accordance with claim 7 further configured to adaptively scale the determined threshold based on a dynamically changing x-ray tube current.

10. A computer program embodied on a computer readable medium for performing a CT imaging scan, said computer program comprising a code segment programmed to control a CT imaging system to:
    scan an anatomy to acquire path-length information;
    determine at least one threshold value during the scan using the acquired path length information; and
    perform a low signal correction on data obtained from scanning the anatomy using the determined threshold value.

11. A computer program in accordance with claim 10 wherein said code segment is further programmed to control a CT imaging system to scan an anatomy to acquire path-length information from at least two orthogonal views.

12. A computer program in accordance with claim 11 wherein said code segment is further programmed to control a CT imaging system to:
    receive at least one application dependent parameter; and
    determine the at least one threshold value using the acquired path length information and the received application dependent parameter.

13. A computer program in accordance with claim 10 wherein said code segment is further programmed to control a CT imaging system to adaptively scale the determined threshold based on a dynamically changing x-ray tube current.

14. A computer program in accordance with claim 10 wherein said code segment is further programmed to control a CT imaging system to adaptively scale the determined threshold based on a dynamically changing bowtie filter shape.

15. A computer program in accordance with claim 10 wherein said code segment is further programmed to control a CT imaging system to perform a low signal correction on data obtained from scanning the anatomy using the determined threshold value, wherein the low signal correction is directionally adaptive.

16. A computer program in accordance with claim 15 wherein said code segment is further programmed to control a CT imaging system to adaptively scale the determined threshold based on a dynamically changing x-ray tube current.

17. A computer program in accordance with claim 10 wherein said code segment is further programmed to control a CT imaging system to perform a low signal correction on data obtained from scanning the anatomy using the determined threshold value, wherein the low signal correction is adaptive to a presence or absence of an anatomy boundary.

18. A computer program in accordance with claim 17 wherein said code segment is further programmed to control a CT imaging system to adaptively scale the determined threshold based on a dynamically changing x-ray tube current.

19. A method for obtaining data, said method comprising:
    scanning an anatomy to acquire path-length information;
    determining at least one threshold value during the scan using the acquired path length information; and performing a low signal correction on data obtained from scanning the anatomy using the determined threshold value.

20. A method in accordance with claim 19 further wherein said scanning an anatomy comprises scanning an anatomy to acquire path-length information from at least two orthogonal views.

21. A method in accordance with claim 20 further comprising receiving at least one application dependent parameter, wherein said determining at least one threshold value comprises using the acquired path length information and the received application dependent parameter.

22. A method in accordance with claim 19 further comprising adaptively scaling the determined threshold based on a dynamically changing x-ray tube current.

23. A method in accordance with claim 19 further comprising adaptively scaling the determined threshold based on a dynamically changing bowtie filter shape.

24. A method in accordance with claim 19 wherein said performing a low signal correction comprises performing a low signal correction on data obtained from scanning the anatomy using the determined threshold value, wherein the low signal correction is directionally adaptive.

25. A method in accordance with claim 24 further comprising adaptively scaling the determined threshold based on a dynamically changing x-ray tube current.

26. A method in accordance with claim 19 wherein said performing a low signal correction comprises performing a low signal correction on data obtained from scanning the anatomy using the determined threshold value, wherein the low signal correction is adaptive to a presence or absence of an anatomy boundary.

27. A method in accordance with claim 26 further comprising adaptively scaling the determined threshold based on a dynamically changing x-ray tube current.

* * * * *